(12) United States Patent
Garabadian et al.

(10) Patent No.: US 8,215,312 B2
(45) Date of Patent: Jul. 10, 2012

(54) THERAPEUTIC MOUTHPIECE FOR TREATING SLEEP DISORDERS

(76) Inventors: Charles Garabadian, Salem, SC (US); Renee McPhee, Atlanta, GA (US)

( * ) Notice: Subject to any disclaimer, the term of this patent is extended or adjusted under 35 U.S.C. 154(b) by 296 days.

(21) Appl. No.: 12/459,710

(22) Filed: Jul. 7, 2009

(65) Prior Publication Data

US 2011/0005526 A1    Jan. 13, 2011

(51) Int. Cl.
*A61F 5/37* (2006.01)
*A61F 5/56* (2006.01)
*A61C 5/14* (2006.01)
*A61C 3/00* (2006.01)
*A61C 5/00* (2006.01)

(52) U.S. Cl. ............ 128/848; 128/846; 128/862; 433/6; 433/7; 433/18; 433/19; 433/24; 433/140; 602/902

(58) Field of Classification Search ................... 433/6, 7, 433/14, 18, 19, 24, 140; 128/846, 848, 859–862; 602/902

See application file for complete search history.

(56) References Cited

U.S. PATENT DOCUMENTS

| | | | | |
|---|---|---|---|---|
| 3,513,838 A * | 5/1970 | Dammermann et al. | ..... | 128/861 |
| 4,376,628 A * | 3/1983 | Aardse | ............. | 433/80 |
| 4,541,800 A | 9/1985 | Bernstein | | |
| 5,499,633 A | 3/1996 | Fenton | | |
| 5,570,704 A | 11/1996 | Buzzard et al. | | |
| 5,794,627 A | 8/1998 | Frantz et al. | | |
| 5,823,193 A | 10/1998 | Singer et al. | | |
| 5,868,138 A | 2/1999 | Halstrom | | |
| 5,884,628 A | 3/1999 | Hilsen | | |
| 5,941,247 A | 8/1999 | Keane | | |
| 6,041,784 A | 3/2000 | Halstrom | | |
| 6,055,986 A | 5/2000 | Meade | | |
| 6,109,265 A | 8/2000 | Frantz et al. | | |
| 6,170,485 B1 | 1/2001 | Orrico | | |
| 6,729,335 B1 | 5/2004 | Halstrom | | |
| 6,983,752 B2 | 1/2006 | Garabadian | | |
| 7,156,774 B2 | 1/2007 | Mohindra | | |
| 7,416,516 B2 | 8/2008 | Mohindra | | |
| 7,766,016 B2 * | 8/2010 | Orrico et al. | .................. | 128/848 |
| 2003/0056797 A1 | 3/2003 | Strong | | |
| 2007/0283967 A1 | 12/2007 | Bailey | | |
| 2009/0090371 A1 | 4/2009 | Toussaint | | |

* cited by examiner

*Primary Examiner* — Patricia Bianco
*Assistant Examiner* — Brandon L Jackson
(74) *Attorney, Agent, or Firm* — McNair Law Firm, P.A.; Seann P. Lahey

(57) ABSTRACT

An upper tray adapted to receive a wearer's maxillary teeth. A lower tray adapted to receive the wearer's mandibular teeth. A first upper ridge is carried on a maxillary occlusal surface of the upper tray. A second upper ridge is carried on the maxillary occlusal surface of the upper tray posterior to and spaced from the first upper ridge. A lower ridge is carried on a mandibular occlusal surface of the lower tray received between the first upper ridge and the second upper ridge. The lower tray is movable to a forward position where the lower ridge abuts the first upper ridge to limit forward movement of the lower tray in relation to the upper tray, and the lower tray is movable to a rearward position where the lower ridge abuts the second upper ridge to limit rearward movement of the lower tray in relation to the upper tray.

17 Claims, 2 Drawing Sheets

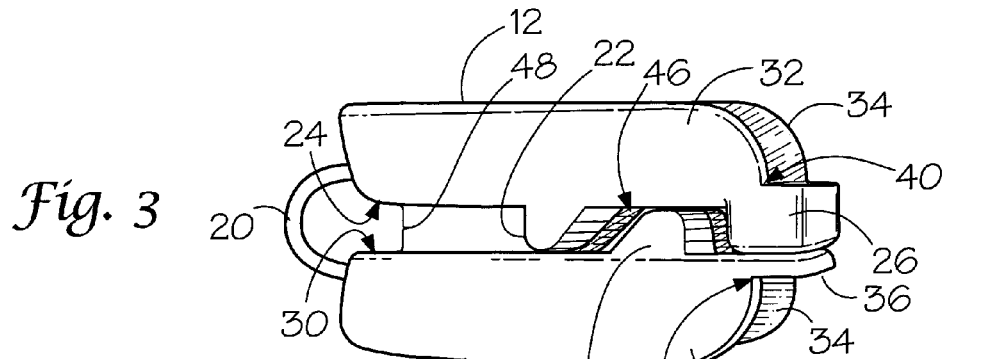
*Fig. 3*
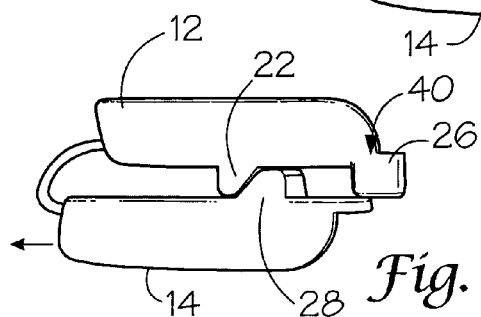
*Fig. 4*
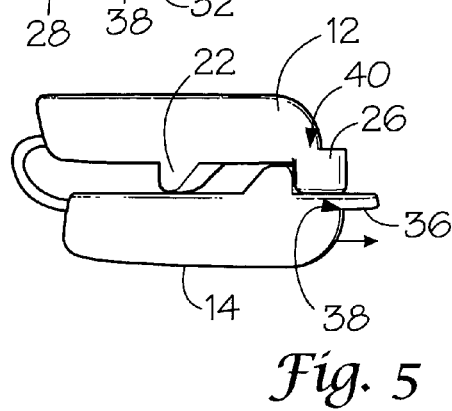
*Fig. 5*
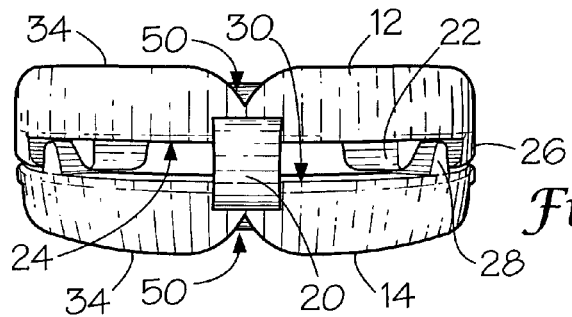
*Fig. 6*
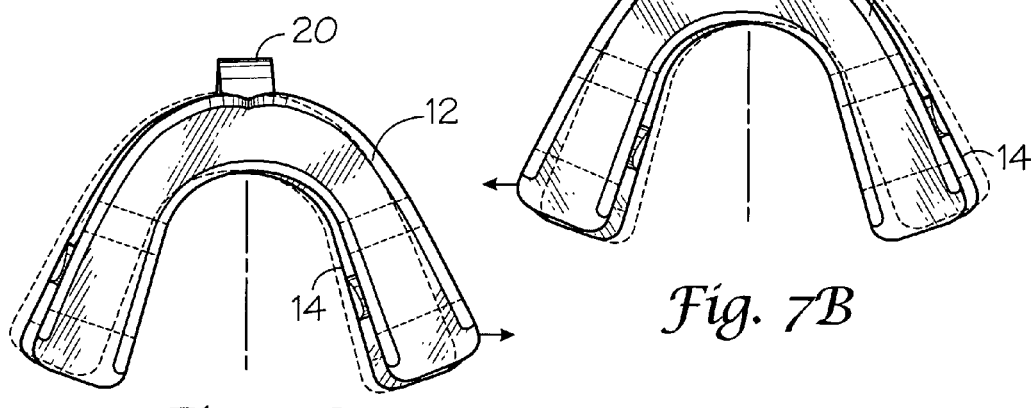
*Fig. 7A*
*Fig. 7B*

THERAPEUTIC MOUTHPIECE FOR TREATING SLEEP DISORDERS

BACKGROUND OF THE INVENTION

1) Field of the Invention

The present invention relates to oral dental appliances, and more particularly, to a therapeutic mouthpiece generally worn during sleep for the prevention and alleviation of sleep disorders such as snoring, clenching, bruxing, and to protect dental work. The mouthpiece spaces the occlusal surfaces of a wearer's maxillary and mandibular teeth and prevents posterior movement of the lower jaw while allowing for limited vertical and lateral movement to adjust to accommodate a variety of wearers.

2) Description of Related Art

It is known in the prior art that an oral appliance which opens the jaws and controls the position of the mandible can help reduce incidences of snoring, sleep apnea, and other breathing problems associated with sleep. While the prior art is replete with such devices, many are uncomfortable due to their rigid construction, which often leads to joint pain in the jaws. Some of the devices represented in the prior art are adjustable to move the jaw forward or back, or adjust the spacing between the jaws, but are still generally rigid devices that set defined positions. Further, these devices are generally not customizable by the user and require professional adjustment to fit the appliance to the user's needs. Additionally, such adjustments typically only modify the appliance to a new fixed position and do not allow for lateral, vertical, and horizontal movement of the jaws to prevent cramping and muscle spasms.

There is no existing appliance that is freely adjustable to accommodate the jaw positions of a variety of users that will allow for vertical and lateral movement, while limiting posterior movement of the mandible. For most appliances, adjustments are made by either soldering on spacers or grinding away plastic from the appliance. Other devices have rigidly arranged blocks or ridges that cooperate to position and prevent movement of the jaws. Such devices have a limited ability to accommodate different user jaw positions due to the predefined relationship of the ridges. Other more adjustable appliances simply advance and space the lower jaw through set incremental steps. Such devices rigidly interlock the maxillary and mandibular portions of the appliance together, preventing any vertical or lateral movement of the jaw, which can be unnecessarily painful to most users. Additionally, many of these devices do not provide an opening at the front of the mouth through which the tongue may extend to prevent airway constriction that causes many of the sleep breathing disorders.

Accordingly, it is an object of the present invention to provide a therapeutic mouthpiece which is adaptable to a wide variety of users without professional adjustment to properly fit the appliance.

It is an object of the present invention to provide a therapeutic mouthpiece which limits both posterior and anterior movement of the mandible to prevent and alleviate sleep disorders.

It is an object of the present invention to provide a therapeutic mouthpiece in which the maxillary and mandibular portions are not rigidly connected and allows for vertical and lateral movement of the jaws to prevent muscle spasms and joint pain.

It is an object of the present invention to provide a therapeutic mouthpiece that produces an unobstructed opening at the front of the mouth through which the tongue is free to extend.

It is an object of the present invention to provide a therapeutic mouthpiece which spaces the occlusal surfaces of a wearer's maxillary and mandibular teeth.

SUMMARY OF THE INVENTION

The above objectives are accomplished according to the present invention by providing a therapeutic mouthpiece comprising an upper tray adapted to receive a wearer's maxillary teeth; a lower tray adapted to receive the wearer's mandibular teeth; a first upper ridge carried on a maxillary occlusal surface of the upper tray; a second upper ridge carried on the maxillary occlusal surface of the upper tray posterior to and spaced from the first upper ridge; a lower ridge carried on a mandibular occlusal surface of the lower tray received between the first upper ridge and the second upper ridge; and, the lower tray movable to a forward position in which the lower ridge abuts the first upper ridge to limit forward movement of the lower tray in relation to the upper tray, and the lower tray movable to a rearward position in which the lower ridge abuts the second upper ridge to limit rearward movement of the lower tray in relation to the upper tray.

In a further embodiment, an occlusal surface extension projects from a distal end of the mandibular occlusal surface of the lower tray. The second upper ridge is carried at a distal end of the maxillary occlusal surface of the upper tray. The second upper ridge is received on the occlusal surface extension when the lower tray is disposed in the forward position.

In a further embodiment, the first upper ridge includes a first slanted engaging surface, and the lower ridge includes a second slanted engaging surface, wherein the first and second slanted engaging surfaces are constructed and arranged to cooperate so that vertical sliding engagement of the first slanted engaging surface against the second slanted engaging surface directs the lower tray in a rearward direction in relation to the upper tray.

In a further embodiment, the space between the first upper ridge and the second upper ridge defines an adjustment gap and the lower ridge is constructed and arranged to slidably engage the maxillary occlusal surface of the upper tray between the first upper ridge and the second upper ridge so that positioning of the lower tray is adjustable relative to the upper tray to accommodate different jaw positions among a variety of wearers.

In a further embodiment, a generally v-shaped notch is disposed in an outer sidewall of at least one of the upper tray and the lower tray generally at a frontal portion of the outer sidewall adapted for receiving a frenum muscle under the wearer's lip and to allow for flexibility in bending the upper and lower tray.

In a further embodiment, the first upper ridge and the second upper ridge are constructed and arranged to engage the mandibular occlusal surface of the lower tray, and the lower ridge is constructed and arranged to engage the maxillary occlusal surface of the upper tray to define a bite gap between the upper tray and the lower tray for maintaining separation between the wearer's maxillary teeth and mandibular teeth.

In a further embodiment, the first upper ridge, the second upper ridge and the lower ridge are constructed from a semi-rigid material that allows each of the ridges to bend when a bite pressure is applied to protect facial muscles from strain while maintaining the general structure of the ridges to provide the bite gap between the upper tray and the lower tray.

In a further embodiment, the bite gap extends generally along a frontal portion of the upper tray and the lower tray providing an opening for allowing forward movement of the wearer's tongue between the upper and lower trays.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 3 shows a side view of the mouthpiece in a neutral position according to the present invention;

FIG. 4 shows a side view of the mouthpiece with the lower tray in a forward position relative to said upper tray according to the present invention;

FIG. 5 shows a side view of the mouthpiece with the lower tray in a rearward position relative to said upper tray according to the present invention;

FIG. 6 shows a front elevation view of the mouthpiece according to the present invention; and, FIGS. 7A and 7B show a top elevation view of the lateral adjustment between the upper and lower trays according to the present invention.

DETAILED DESCRIPTION OF A PREFERRED EMBODIMENT

Figure 1:
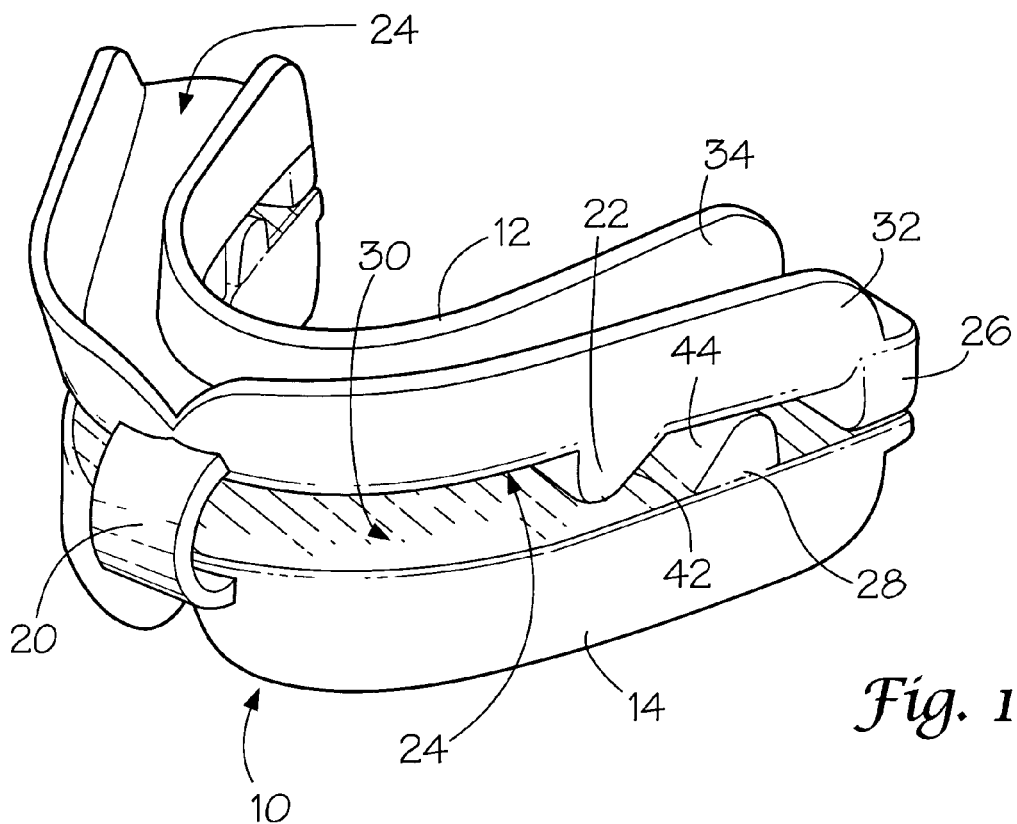
FIG. 1 shows a perspective view of the mouthpiece according to the present invention.

With reference to the drawings, the invention will now be described in more detail. Referring to FIG. 1, a therapeutic mouthpiece, designated generally as 10, is shown that can space the occlusal surfaces of a wearer's maxillary and mandibular teeth and limit posterior and anterior movement of the mandible, while allowing for vertical and lateral movement. Mouthpiece 10 includes an upper tray 12 adapted to receive a wearer's maxillary teeth of the upper jaw, and a lower tray 14 adapted to receive the wearer's mandibular teeth of the lower jaw.

Figure 2:
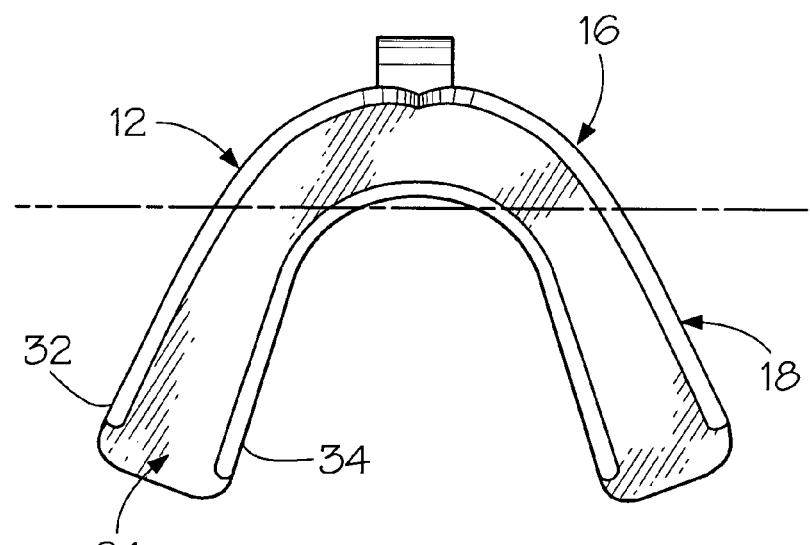
FIG. 2 shows a top elevation view of the mouthpiece according to the present invention.

With further reference to FIGS. 2 and 6, both upper tray 12 and lower tray 14 are defined as having an anterior or frontal portion, designated generally as 16, which receives the teeth along the front of the jaws, and a posterior portion, designated generally as 18, which receives the teeth along the rearward portions of the jaws. Preferably, the trays are made of FDA approved EVA (ethylene vinyl acetate) material or other commonly known plastic used by those skilled in the art. However, the trays are not limited to being made of a specific plastic, but rather may be made of any material suitable to carrying out the present invention. In a preferred embodiment, upper tray 12 and lower tray 14 are moldable to conform to the, shape of the wearer's maxillary and mandibular dentitions and adapt to the generally alignment of the teeth along the upper and lower jaws, respectively. Providing trays 12 and 14 in an easily moldable yet durable material helps to match the shape of the wearer's teeth and establish a custom fit which is more comfortable for the wearer and holds the trays in place against the teeth in a much more effective manner than if the trays are not molded to the shape of the wearer's teeth. The EVA material is preferred as it softens at approximately 145° F. Thus, the mouthpiece can be fitted by the general public through a simple warming of the device, such as in hot water, without the need for professional fitting.

A flexible connector strip 20 may be provided to interconnect the upper and lower trays. However, depending on the fitting needs, the wearer's comfort issues, and the desired use, the mouthpiece can be provided without connector strip 20 to enhance the universal nature of the mouthpiece. Also, the mouthpiece can be used right-side-up as illustrated, or it can be used up-side-down with no general change in the operation of the mouthpiece. Some user's may simply prefer the mouthpiece in one orientation or the other.

Referring to FIG. 3, a first upper ridge 22 is carried on and projects downwardly from a maxillary occlusal surface, designated generally as 24, of upper tray 12. A second upper ridge 26 is carried on and projects downwardly maxillary occlusal surface 24 of the upper tray posterior to and spaced from the first upper ridge. Accordingly, the second upper ridge 26 is disposed in a more rearward position along the upper jaw in relation to first upper ridge 22 when positioned in the wearer's mouth. In the illustrated embodiment, both first upper ridge 22 and second upper ridge 26 are carried on maxillary occlusal surface 24 in posterior portion 18. The ridges are duplicated on both left and right sides of the mouthpiece to provide uniformity in contact when bite pressure is applied by the wearer to engage the upper and lower trays.

A lower ridge 28 is carried on and projects upwardly from a mandibular occlusal surface, designated generally as 30, of lower tray 14. Lower ridge 28 is positioned on mandibular occlusal surface 30 to be received between first upper ridge 22 and second upper ridge 26 when the trays are positioned and engaged in the wearer's mouth. The ridges are constructed and arranged to limit the anterior and posterior movement of the mandible through the engagement of the lower ridge with the upper ridges. Referring to FIG. 4, lower tray 14 is movable to a forward position in which lower ridge 28 abuts first upper ridge 22 to limit forward movement of lower tray 14 in relation to upper tray 12. Further, referring to FIG. 5, lower tray 14 is movable to a rearward position in which lower ridge 28 abuts second upper ridge 26 to limit rearward movement of lower tray 14 in relation to upper tray 12.

Referring to FIG. 2 both upper tray 12 and lower tray 14 include an outer sidewall 32 and an inner sidewall 34 interconnected by maxillary occlusal surface 24 on upper tray 12 and by mandibular occlusal surface 30 on lower tray 14. Referring to FIGS. 3-5, an occlusal surface extension 36 projects rearwardly from a distal end, designated generally as 38, of mandibular occlusal surface 30 beyond outer sidewall 32 and inner sidewall 34 of lower tray 14. The second upper ridge 26 is also carried at a distal end, designated generally as 40, of maxillary occlusal surface 24 of upper tray 12. When located in the wearer's mouth, second upper ridge 26 may be received on occlusal surface extension 36 when lower tray 14 is disposed in the forward position, represented in FIG. 4. Occlusal surface extension 36 maintains a uniform and level engagement of the ridges when in the forward position to avoid second upper ridge 26 from directly contacting a wearer's teeth. Regardless of the distal end point for outer sidewall 32 and inner sidewall 34, which can be varied, the effect of the construction and arrangement between the trays is that second upper ridge 26 should always rest on the mandibular occlusal surface 30, or any defined extension thereof such as occlusal surface extension 36, to maintain uniform engagement of the ridges between the trays.

Referring to FIG. 1, first upper ridge 22 includes a first slanted engaging surface 42, and lower ridge 28 includes a second slanted engaging surface 44. First and second slanted engaging surfaces 42 and 44 are constructed and arranged to cooperate so that vertical sliding engagement of first slanted engaging surface 42 against second slanted engaging surface 44, such as when closing the jaws together, directs lower tray 14 in a rearward direction in relation to upper tray 12. The slanted surface 42 and 44 help to prevent a rigid engagement of the first upper ridge and lower ridge that would prevent first upper ridge 22 from engaging mandibular occlusal surface 30 and lower ridge 28 from engaging maxillary occlusal surface 24.

Referring to FIG. 3, the spacing between first upper ridge 22 and second upper ridge 26 defines an adjustment gap, designated generally as 46. Lower ridge 28 is received between first upper ridge 22 and second upper ridge 26 so that lower ridge 28 is free to engage maxillary occlusal surface 24 of upper tray 12 within adjustment gap 46. First upper ridge 22 and second upper ridge 26 are free to engage mandibular occlusal surface 30 of lower tray 14. Together, the ridges maintain a vertical separation, or bite gap 48, between the maxillary occlusal surface and the mandibular occlusal surface of the trays. Accordingly, maxillary occlusal surface 24 is prevented from direct engagement with mandibular occlusal surface 30.

Further, in the illustrated embodiment, lower ridge 28 is constructed and arranged to slidably engage along maxillary occlusal surface 24 of upper tray 12 between first upper ridge 22 and second upper ridge 26 so that positioning of the lower tray is adjustable in a horizontal direction as shown in FIGS. 4 and 5. Additionally, referring to FIGS. 7A and 7B, because the upper and lower trays are not rigidly connected, they are also adjustable in a lateral direction relative to the upper tray. Providing for both horizontal and lateral adjustments will help to accommodate different jaw positions among a variety of wearers to increase comfort and fit abilities not found in existing prior art devices. Engagement of the ridges in the forward and rearward positions (FIG. 4 and FIG. 5) prevents posterior or anterior movement of the wearer's mandible in excess of the spacing defined in adjustment gap 46. Allowing for some horizontal, lateral and vertical flexibility relieves the wearer's jaw muscles of stress, and generally provides for a much more comfortable and user friendly dental appliance.

In a preferred embodiment, first upper ridge 22, second upper ridge 26 and lower ridge 28 are constructed from a semi-rigid material, such as EVA mentioned above, that allows each of the ridges to bend when a bite pressure is applied to protect facial muscles from strain while maintaining the general structure of the ridges to provide bite gap 48 between upper tray 12 and lower tray 14. Preferably, the vertical separation between the trays defined as bite gap 48 extends generally along frontal portion 16 between upper tray 12 and lower tray 14 providing an opening for allowing forward movement of the wearer's tongue between the upper and lower trays.

In a further embodiment, referring to FIG. 6, the mouthpiece includes a generally v-shaped notch 50 disposed in outer sidewall 34 of at least one of upper tray 12 and lower tray 14 generally at a midpoint of frontal portion 16 of outer sidewall 34 adapted for receiving a frenum muscle under the wearer's lip and to allow for flexibility in bending the upper and lower tray for improved fit and comfort.

While a preferred embodiment of the invention has been described using specific terms, such description is for illustrative purposes only, and it is to be understood that changes and variations may be made without departing from the spirit or scope of the following claims.

What is claimed is:

1. A therapeutic mouthpiece comprising:
an upper tray adapted to receive a wearer's maxillary teeth;
a lower tray adapted to receive said wearer's mandibular teeth;
a first upper ridge carried on a maxillary occlusal surface of said upper tray;
a second upper ridge carried on said maxillary occlusal surface of said upper tray posterior to and spaced from said first upper ridge;
a lower ridge carried on a mandibular occlusal surface of said lower tray received between said first upper ridge and said second upper ridge in an unsecured arrangement so that said lower ridge slides freely forward and back between said first upper ridge and said second upper ridge while continuously in contact with said maxillary occlusal surface of said upper tray; and,
whereby said lower tray is movable to a forward position in which said lower ridge slides forward and abuts said first upper ridge to limit forward movement of said lower tray in relation to said upper tray during use without disengaging said lower ridge from said maxillary occlusal surface of said upper tray, and said lower tray is movable to a rearward position in which said lower ridge slides rearward and abuts said second upper ridge to limit rearward movement of said lower tray in relation to said upper tray during use without disengaging said lower ridge from said maxillary occlusal surface of said upper tray.

2. The mouthpiece of claim 1 including an occlusal surface extension projecting from a distal end of said mandibular occlusal surface of said lower tray.

3. The mouthpiece of claim 2 wherein said second upper ridge is carried at a distal end of said maxillary occlusal surface of said upper tray.

4. The mouthpiece of claim 3 wherein said second upper ridge is received on said occlusal surface extension when said lower tray is disposed in said forward position.

5. The mouthpiece of claim 1 wherein said first upper ridge and said second upper ridge are constructed and arranged to engage said mandibular occlusal surface of said lower tray, and said lower ridge is constructed and arranged to engage said maxillary occlusal surface of said upper tray to define a bite gap between said upper tray and said lower tray for maintaining separation between said wearer's maxillary teeth and mandibular teeth.

6. The mouthpiece of claim 5 wherein said first upper ridge, said second upper ridge and said lower ridge are constructed from a semi-rigid material that allows each of said ridges to bend when a bite pressure is applied to protect facial muscles from strain while maintaining the general structure of said ridges to provide said bite gap between said upper tray and said lower tray.

7. The mouthpiece of claim 5 wherein said bite gap extends generally along a frontal portion of said upper tray and said lower tray providing an opening for allowing forward movement of the wearer's tongue between said upper and lower trays.

8. The mouthpiece of claim 1 wherein said first upper ridge includes a first slanted engaging surface, and said lower ridge includes a second slanted engaging surface, wherein said first and second slanted engaging surfaces are constructed and arranged to cooperate so that vertical sliding engagement of said first slanted engaging surface against said second slanted engaging surface directs said lower tray in a rearward direction in relation to said upper tray.

9. The mouthpiece of claim 1 wherein said space between said first upper ridge and said second upper ridge defines an adjustment gap and wherein said lower ridge is constructed and arranged to slidably engage said maxillary occlusal surface of said upper tray between said first upper ridge and said second upper ridge so that positioning of said lower tray is adjustable relative to said upper tray to accommodate different jaw positions among a variety of wearers.

10. The mouthpiece of claim 1 including a generally v-shaped notch disposed in an outer sidewall of at least one of said upper tray and said lower tray generally at a frontal portion of said outer sidewall adapted for receiving a frenum muscle under the wearer's lip and to allow for flexibility in bending said upper and lower tray.

11. A therapeutic mouthpiece comprising:
an upper tray for receiving a wearer's maxillary teeth;
a lower tray for receiving said wearer's mandibular teeth;
a first upper ridge projecting downward from a maxillary occlusal surface of said upper tray;
a second upper ridge carried generally at a distal end portion of said upper tray projecting downward from said maxillary occlusal surface of said upper tray, wherein said first upper ridge and said second upper ridge are spaced along said maxillary occlusal surface to define an adjustment gap;
a lower ridge projecting upward from a mandibular occlusal surface of said lower tray;
wherein said lower ridge is received between said first upper ridge and said second upper ridge so that said lower ridge is free to engage said maxillary occlusal surface of said upper tray within said adjustment gap, and said first upper ridge and said second upper ridge are free to engage said mandibular occlusal surface of said lower tray to maintain a vertical separation between said maxillary occlusal surface and said mandibular occlusal surface of said trays; and,
wherein said lower ridge is received between said first upper ridge and said second upper ridge in an unsecured arrangement so that said lower ridge slides freely forward and back between said first upper ridge and said second upper ridge while continuously in contact with said maxillary occlusal surface to move within said adjustment gap so that positioning of said lower tray is continuously adjustable during use in a horizontal and a lateral direction relative to said upper tray without disengaging said lower ridge from said maxillary occlusal surface of said upper tray to accommodate different jaw positions among a variety of wearers while preventing posterior or anterior movement of said wearer's mandible in excess of said adjustment gap.

12. The mouthpiece of claim 11 including an occlusal surface extension projecting from a distal end of said mandibular occlusal surface of said lower tray.

13. The mouthpiece of claim 12 wherein said second upper ridge is received on said occlusal surface extension when said lower tray is disposed in a forward position in which said lower ridge abuts said first upper ridge.

14. The mouthpiece of claim 11 wherein said first upper ridge, said second upper ridge and said lower ridge are constructed from a semi-rigid material that allows each of said ridges to bend when a bite pressure is applied to protect facial muscles from strain while maintaining the general structure of said ridges to maintain said vertical separation between said upper tray and said lower tray.

15. The mouthpiece of claim 14 wherein said vertical separation extends generally along a frontal portion of said upper tray and said lower tray providing an opening for allowing forward movement of the wearer's tongue between said upper and lower trays.

16. The mouthpiece of claim 11 wherein said first upper ridge includes a first slanted engaging surface, and said lower ridge includes a second slanted engaging surface, wherein said first and second slanted engaging surfaces are constructed and arranged to cooperate so that vertical sliding engagement of said first slanted engaging surface against said second slanted engaging surface directs said lower tray in a rearward direction in relation to said upper tray.

17. The mouthpiece of claim 11 including a generally v-shaped notch disposed in an outer sidewall of at least one of said upper tray and said lower tray generally at a frontal portion of said outer sidewall adapted for receiving a frenum muscle under the wearer's lip and to allow for flexibility in bending said upper and lower tray.

* * * * *